(12) United States Patent
Motoyoshi et al.

(10) Patent No.: US 8,229,539 B1
(45) Date of Patent: Jul. 24, 2012

(54) BRAIN PROBE AND METHOD FOR MANUFACTURING SAME

(75) Inventors: Makoto Motoyoshi, Sendai (JP); Mitsumasa Koyanagi, Sendai (JP); Hajime Mushiake, Sendai (JP); Tetsu Tanaka, Sendai (JP); Norihiro Katayama, Sendai (JP)

(73) Assignees: Tohoku-Microtec Co., Ltd., Miyagi (JP); Tohoku University, Miyagi (JP)

( * ) Notice: Subject to any disclaimer, the term of this patent is extended or adjusted under 35 U.S.C. 154(b) by 0 days.

(21) Appl. No.: 13/207,715

(22) Filed: Aug. 11, 2011

Related U.S. Application Data

(63) Continuation of application No. PCT/JP2011/054246, filed on Feb. 25, 2011.

(51) Int. Cl.
*A61B 5/0478* (2006.01)
*A61B 1/05* (2006.01)
*H01R 43/00* (2006.01)

(52) U.S. Cl. ............... 600/378; 607/116; 29/825

(58) Field of Classification Search .................. 600/378; 607/116
See application file for complete search history.

(56) References Cited

U.S. PATENT DOCUMENTS

| | | | |
|---|---|---|---|
| 5,515,848 A * | 5/1996 | Corbett et al. | 600/377 |
| 7,190,989 B1 * | 3/2007 | Swanson et al. | 600/378 |

| | | | |
|---|---|---|---|
| 2008/0243214 A1 | 10/2008 | Koblish | |

FOREIGN PATENT DOCUMENTS

| | | |
|---|---|---|
| JP | 2000-325320 | 11/2000 |
| JP | 2010-522623 | 7/2010 |
| JP | 2011-036360 | 2/2011 |
| WO | 2009075625 A1 | 6/2009 |

OTHER PUBLICATIONS

Kobayashi et al., Japanese Journal of Applied Physics, Development of Si Double-Sided Microelectrode for Platform of Brain Signal Processing System, 2009, vol. 48, p. 04C194-1-04C194-5.

* cited by examiner

*Primary Examiner* — Lee Cohen
(74) *Attorney, Agent, or Firm* — Rothwell, Figg, Ernst & Manbeck, P.C.

(57) ABSTRACT

A brain probe includes: a core probe made from a metal; and n electrode plates attached so as to cover an entire side surface circumference of the core probe and forming n side planes providing an n-angular cross section (n is an integer equal to or greater than 3). Each of the electrode plates is manufactured by a LSI manufacturing process, and provided with at least one electrode and a lead-out wiring extending in a longitudinal direction of a side plane from each of the at least one electrode.

14 Claims, 12 Drawing Sheets

V-SHAPED GROOVE

12

FIG. 13D (111)plane

FIG. 13C (100)plane

FIG. 13E (100)plane (111)plane 54.74°

BRAIN PROBE AND METHOD FOR MANUFACTURING SAME

CROSS-REFERENCE TO RELATED APPLICATIONS

This application is a continuation of international application PCT/JP2011/54246, filed on Feb. 25, 2011.

TECHNICAL FIELD

The present invention relates to a brain probe that detects electric signals from the brain cells and outputs electric signals stimulating the brain cells, and the present invention also relates to a method for manufacturing the same.

BACKGROUND ART

The aging of society in recent years is accompanied by the increase in the number of patients with developed diseases (for example, Parkinson disease, and paralysis, epilepsy) caused by brain disorder. Clarification of brain functions, in particular clarification of nerve circuit activity inside the brain is an indispensible means for developing methods for treating the diseases caused by brain disorder. Brain probes that are inserted into the brain to detect electric signals (brain waves) of brain cells have been used for such purpose. Furthermore, the brain probes can be also used as a means for supplying electric stimulation into the brain in order to specify the location in which the brain disorder has occurred in the treatment of diseases caused by brain disorder.

Further, in recent years, brain probes have also found use as medical tools providing electric stimulation to restore the brain functions, and clinical tests have also been conducted on humans as part of the BMI (Brain-Machine Interface) or BCI (Brain-Computer Interface) research.

BMI is a system with indirect brain-machine interaction and can be generally classified into motion-type BMI, sensation-type BMI, and direct operation BMI. The motion-type BMI is a technique for detecting and using the activity representing the motion output, from among various types of neural activity of the brain, and controlling an external device such as a robot. Such a technique is used, for example, for motion function rehabilitation in quadriplegic patients. The sensation-type BMI is a technique for transmitting signals into the brain and inducing and enhancing various sensations. Some of the sensation-type BMI have already found practical use, representative examples thereof including artificial inner ear and artificial retina. The direct operation BMI is a technique for restoring various damaged functions by direct stimulation inside the brain.

The BCI is a general term for an interface that directly connects electric signals flowing inside the human brain with a computer, thereby making it possible to operate the computer by thoughts. The BCI includes a technique by which brain wave signals are read on the head surface by using a hat-like electrode, and a technique by which an electrode is directly inserted into the brain and neuron activity is read as signals.

A variety of drug treatment methods are used for treating the Parkinson disease, but the effect of the drug treatment methods is lost after a long time and side effects are sometimes demonstrated. With respect to patients for whom the drug treatment is ineffective, DBS (Deep Brain Stimulation) for stimulating the cerebrum basal ganglia becomes a treatment of choice.

In a brain probe that is inserted into the brain for detecting electric signals inside the brain and providing electric stimulation to the brain, for example, as disclosed in the below-described Non-Patent Document 1, an electrode is disposed on a tip of a fine probe made of silicon and having a diameter of about several hundreds of microns by using a LSI (Large Scale Integration) manufacturing technique, and the electrode is connected by a lead-out wiring to a bonding pad on the other end side for connection to an external device. Further, the brain probe suggested in Non-Patent Document 1 is configured to have a length (above 40 mm) sufficient to reach the basal ganglia in the deep portions of cerebrum and have electrodes on both planes, rather than one plane, of the tip portion thereof. By disposing the electrodes on both planes, it is possible to detect electric signals from both sides of the brain probe.

Non-Patent Document 1: Japanese Journal of Applied Physics 48 (2009) 04C194.

However, the brain probe described in Non-Patent Document 1 has the following drawbacks. Thus, since the entire brain probe described in Non-Patent Document 1 is formed from a silicon substrate, the brain probe is brittle and cannot be inserted individually when inserted deeply into the brain, for example, to the basal ganglia. The brain probe described in Non-Patent Document 1 is guided into the brain by additionally using a metal tube, inserting the metal tube into the brain, and then inserting the brain probe described in Non-Patent Document 1 into the metal tube.

Further, since the brain probe of the Non-Patent Document 1 is oriented by the frontal direction (normal direction) of the planes (front plane, rear plane), the electric signal from the frontal direction is received with better sensitivity than the electric signal from the horizontal direction and sufficient reception sensitivity cannot be obtained for the entire circumference of the brain probe. Thus, the problem is that although the electrodes are disposed on both surfaces, electric signals from specific directions cannot be received with sufficient sensitivity.

SUMMARY OF THE INVENTION

Accordingly, it is an object of the present invention to provide an omnidirecitonal brain probe and method manufacturing for same, that can be individually inserted to the deep portions of the brain and can detect electric signals with better sensitivity over the entire region.

In order to attain the abovementioned object, the present invention provides a brain probe including: a core probe made from a metal; and n electrode plates attached so as to cover an entire side surface circumference of the core probe, and forming n side planes providing an n-angular cross section (n is an integer equal to or greater than 3), wherein at least one electrode and a lead-out wiring extending in a longitudinal direction of the side plane from each of the at least one electrode are provided at each of the electrode plates.

Since a metal core probe is used, the core probe has a sufficient strength enabling the insertion to the deep portions of the brain, and since three or more electrode plates are provided on side planes, good sensitivity is obtained over the entire 360° region in one insertion and an omnidirecitonal brain probe is realized.

The configuration is preferred in which the core probe has a tapered portion that is tapered to a tip and an equidiametric portion extending from the tapered portion toward the other end, a diameter of the equidiametric portion is less than a maximum diameter of the tapered portion, and a diameter of the equidiametric portion in which the electrode plates have been covered on the side surface of the core probe is substantially equal to or less than the maximum diameter of the tapered portion. By reducing a step between the tapered portion and the equidiametric portion, it is possible to inhibit invasiveness.

For example, the electrode plate has a silicon substrate. By using a silicon substrate, it is possible to manufacture the electrode plate by a LSI manufacturing process.

It is preferred that the electrode plates have six planes. The six planes make it possible to prepare two sets each including three electrode plates that realize an omnidirecitonal configuration. Another advantage is that anisotropic etching of a silicon single crystal can be used in the manufacture of electrode plates.

For example, each of the n (equal to or greater than 3) electrode plates is either a first electrode plate having a plurality of electrodes arranged in a first arrangement pattern or a second electrode plate having a plurality of electrodes arranged in a second arrangement pattern different from the first arrangement pattern. The electrode plates with different arrangement patterns can be used according to the application and object. For example, when n is 6, the first electrode plate and the second electrode plate are arranged alternately on the core probe so as to form three side planes of the first electrode plate and three side planes of the second electrode plate.

Alternatively, for example, each of the n electrode plates is one of a first electrode plate having a plurality of electrodes arranged in a first arrangement pattern, a second electrode plate having a plurality of electrodes arranged in a second arrangement pattern different from the first arrangement pattern, and a third electrode plate having a plurality of electrodes arranged in a third arrangement pattern different from the first arrangement pattern and the second arrangement pattern. Similarly to the above-described configuration, the electrode plates with different arrangement patterns can be used according to the application and object. For example, when n is 6, a pair of the first electrode plates, a pair of the second electrode plates, and a pair of the third electrode plates are arranged on the core probe, with the paired plates of the same type facing each other.

The brain probe may further include a signal processing circuit that performs predetermined signal processing with respect to signals from the electrodes and signals outputted to the electrodes, and is connected to the lead-out wirings extending from the electrodes. It is preferred that the electrode plate have a silicon substrate, and the signal processing circuit be formed on the silicon substrate. As a result, the signal processing circuit and the brain probe can be integrated.

A method for manufacturing a brain probe in accordance with the present invention includes the steps of: manufacturing n (n is an integer equal to or greater than 3) electrode plates, each having at least one electrode and a lead-out wiring extending from each of the at least one electrode; and attaching the electrode plates to an entire side surface circumference of a metal core probe so as to form n side planes providing an n-angular cross section (n is an integer equal to or greater than 3).

Since a metal core probe is used, the core probe has a sufficient strength enabling the insertion to the deep portions of the brain, and since three or more electrode plates are provided on side planes, good sensitivity is obtained over the entire 360° region in one insertion and an omnidirecitonal brain probe is realized.

The n electrode plates are manufactured to be connected by long side portions thereof and attached by winding on the side surface of the core probe. As a result, the attachment of a plurality of electrode plates is facilitated.

Further, the n electrode plates are manufactured to be connected by long side portions thereof by using a silicon substrate, and grooves are formed by anisotropic etching at boundaries between adjacent electrode plates. The grooves can be easily formed at the boundaries of connected electrode plates by using the anisotropic etching ability of silicon single crystals.

Preferably, the n electrode plates are manufactured by using a silicon substrate, and a signal processing circuit that performs predetermined signal processing with respect to signals from the electrodes and signals outputted to the electrodes, and is connected to the lead-out wirings extending from the electrodes is formed on the silicon substrate of each of the electrode plates. In this case, the signal processing circuit can be manufactured simultaneously with the manufacture of electrode plates, and the signal processing circuit and brain probe can be integrated.

In accordance with the present invention, it is possible to obtain an omnidirecitonal brain probe that can be inserted individually to the deep portions of the brain and can detect and output electric signals with higher reception sensitivity over the entire circumference, without a spread in sensitivity caused by orientation.

DETAILED DESCRIPTION

The embodiments of the present invention will be described below with reference to the appended drawings. However, the embodiments place no limitation on the technical scope of the present invention.

Figure 1A:
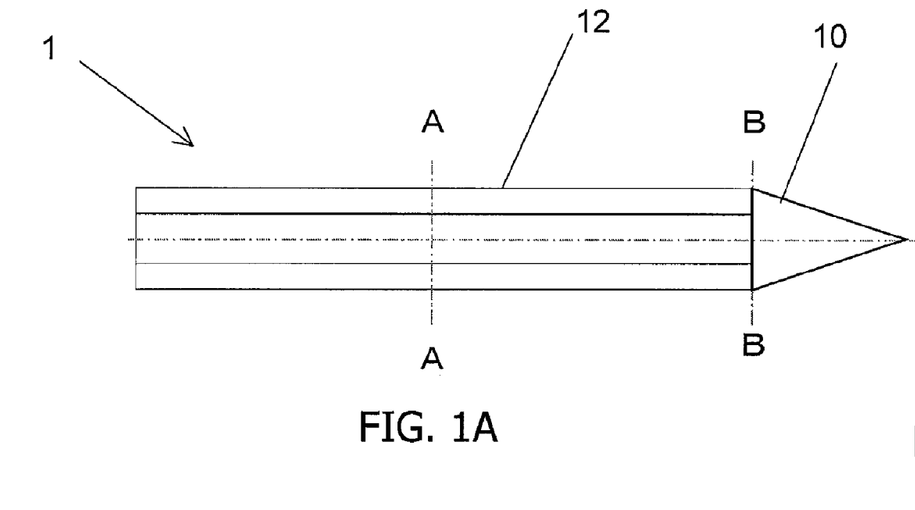
FIG. 1A to FIG. 1C show configuration examples of the brain probe of an embodiment of the present invention.
Figures 1B, 1C:
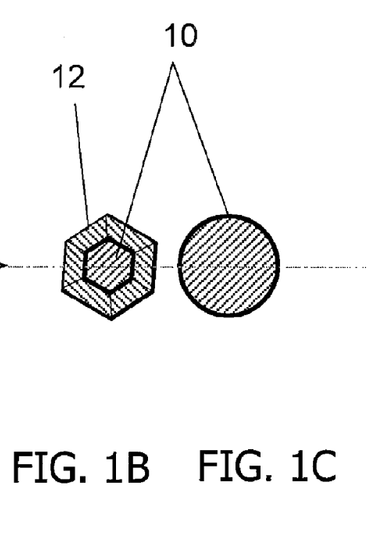

FIG. 1A to FIG. 1C show configuration examples of the brain probe of an embodiment of the present invention. FIG. 1A is a schematic view of the brain probe. FIG. 1B is a cross-sectional view taken along the A-A line in FIG. 1A. FIG. 1C is a cross-sectional view taken along the B-B line in FIG. 1A.

The brain probe 1 is configured to have a core probe 10 and a plurality of electrode plates 12 that cover the side surface of the core probe 10 and are attached to the side surface of the core probe 10 so that the side surface thereof forms a hexagon. By using a hexagonal configuration of electrode plates it is possible to eliminate the spread of reception sensitivity caused by orientation, as compared with a biplane configuration, and realize an omnidirecitonal brain probe in which good reception sensitivity is obtained over the entire circumference. The omnidirecitonal brain probe can study neural activity of a very small area and adjust a stimulation position with respect to a very small area. An omnidirecitonal configuration requires electrode plates on three or more planes, but from the standpoint of the below described manufacturing process and usability, hexagon electrode plates are most preferred.

The core probe 10 is made from a metal having a hardness sufficient for insertion deep into the brain, for example, tungsten or a platinum-tungsten alloy, but may be also manufactured from other metals and alloys that are hard and easily processable. As described hereinbelow, the electrode plate 12 has at least one electrode on each side surface thereof and a lead-out wire extending in the longitudinal direction of the side surface from each electrode.

Figure 2A:
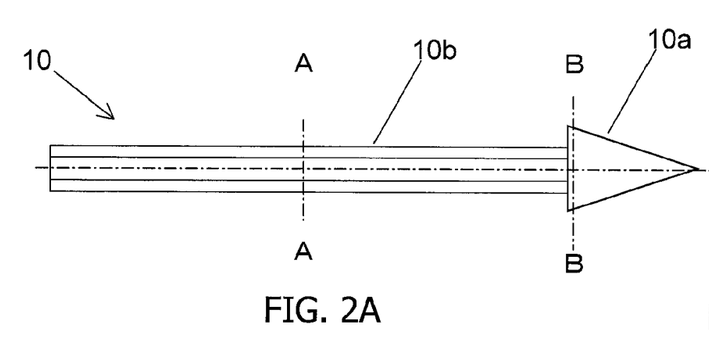
FIG. 2A to FIG. 2C show shape examples of the core probe 10.
Figures 2B, 2C:
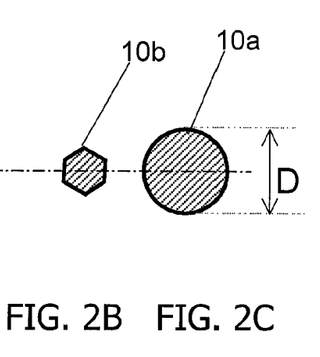
Figure 3A:
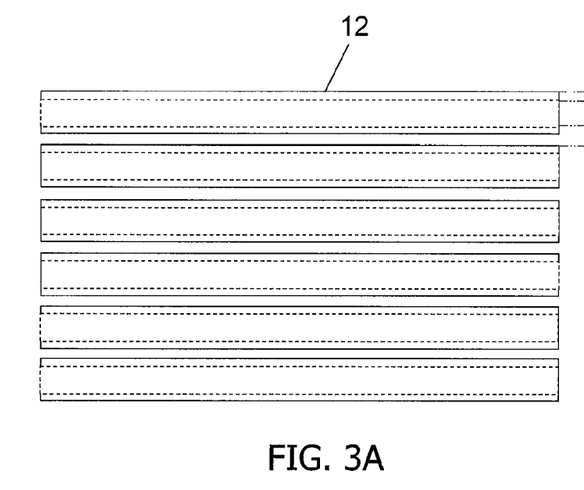
FIG. 3A and FIG. 3B show shape examples of the electrode plate 12.
Figure 3B:
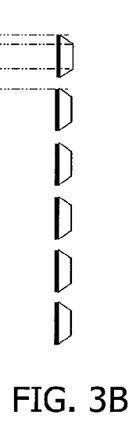

FIG. 2A to FIG. 2C show shape examples of the core probe 10. FIG. 3A and FIG. 3B show shape examples of the electrode plate 12. FIG. 2A is a schematic view of the core probe 10. FIG. 2B is a cross-sectional view taken along the A-A line in FIG. 2A. FIG. 2C is a cross-sectional view taken along the B-B line of FIG. 2A. FIG. 3A is a plan view of six electrode plates 12. FIG. 3B is a cross-sectional view of six electrode plates.

Referring to FIG. 2A to FIG. 2C, the core probe 10 has a tapered portion 10a that is tapered toward the tip and an equidiametric portion 10b extending from the tapered portion toward the other end. The dimensions are, for example, as follows: the total length of the core probe 10 is about 40 mm, the maximum diameter D of the tapered portion 10a is about 200 μm, and the equidiametric portion 10b is about 140 μm. The equidiametric portion 10b is formed by polishing the side surface corresponding to the equidiametric portion 10b in a core probe with a round cross section (diameter 200 μm) and tapered core. As for the dimensions, a length such that the cerebrum basal ganglia could be reached and a diameter as small as possible to ensure low invasiveness are preferred. In the present invention, the core is a metal probe and electrode plates with silicon substrates are attached to the circumference thereof, thereby ensuring the strength enabling the insertion of the brain probe deep into the cerebrum basal ganglia.

The tapered portion 10a has a conical shape and a round cross section. The equidiametric portion 10b is provided with the abovementioned six side planes. Thus, the equidiametric portion 10b has a hexagonal cross section, as shown in FIG. 2A. The electrode plate 12 has an elongated rectangular shape and the cross section of the electrode plate 12 is formed as a trapezoid, as shown in FIG. 3B so that the cross section of the equidiametric portion 10b having the electrode plates attached thereto also be hexagonal. The six electrode plates 12 are attached at respective side surfaces thereof with an adhesive. The equidiametric portion 10b is preferably formed to have a hexagonal shape matching that of the electrode plates 12, but such a configuration is not limiting. For example, the equidiametric portion may have a round cross section. The gaps appearing when the electrode plates 12 are attached can be filled with the adhesive.

Figure 4A:
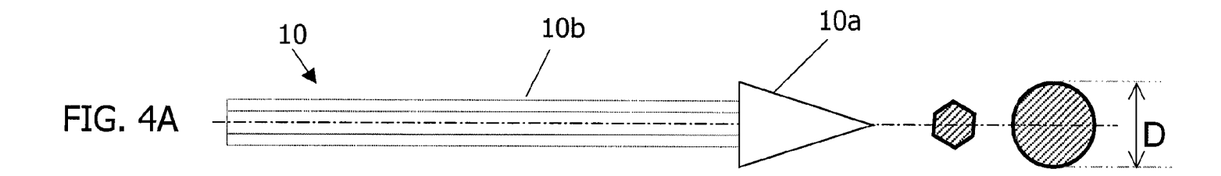
FIG. 4A to FIG. 4C illustrate the processing of attaching the electrode plates 12 to the side surface of the core probe 10.
Figure 4B:
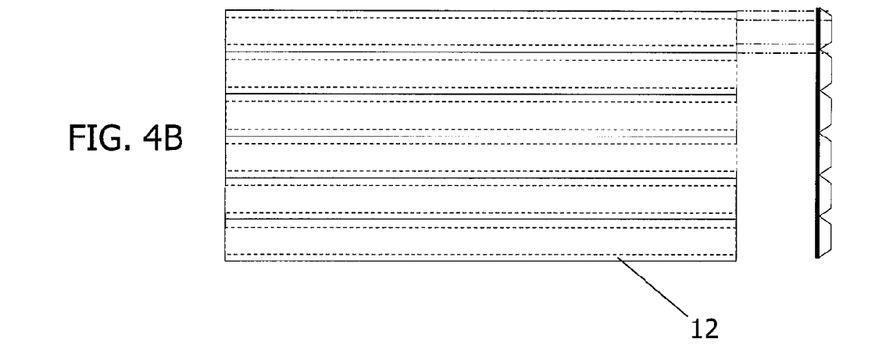
Figure 4C:
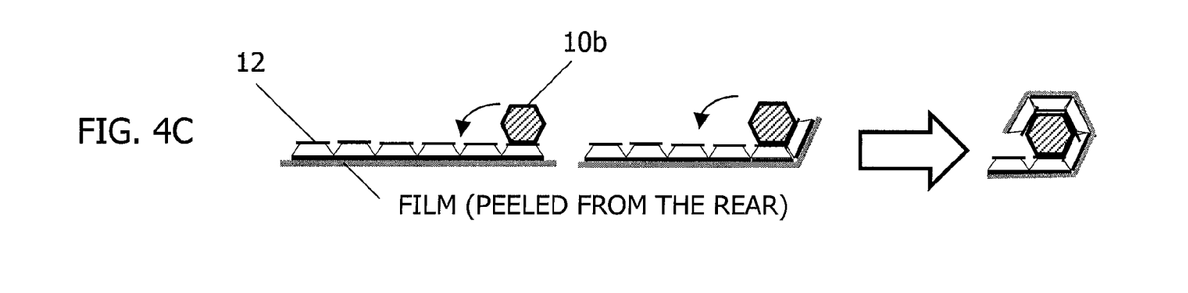

FIG. 4A to FIG. 4C illustrate the processing of attaching the electrode plates 12 to the side surface of the core probe 10. A total of six electrode plates 12 connected to each other by long-side portions are formed, as shown in FIG. 4B, and the electrode plates can be attached by winding on the side surface of the equidiametric portion 10b (see FIG. 4A) of the core probe 10, as shown in FIG. 4C. It goes without saying that the six electrode plates 12 may be produced one by one and attached individually, one by one, to the side surface of the equidiametric portion 10b of the core probe 10.

Figure 5:
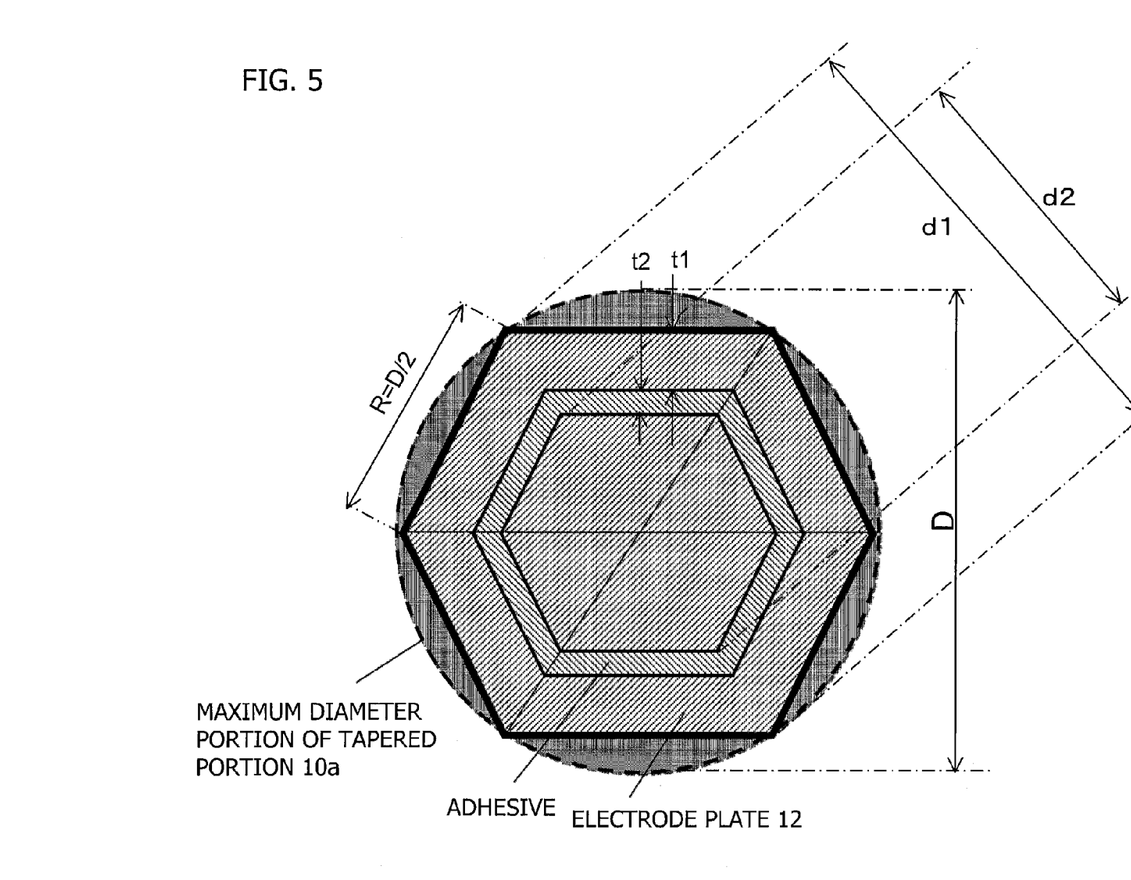
FIG. 5 is an enlarged cross-sectional view of the equidiametric portion 10b having the electrode plates 12 attached thereto.

FIG. 5 is an enlarged cross-sectional view of the equidiametric portion 10b having the electrode plates 12 attached thereto. The equidiametric portion 10b has a regular hexagonal cross section and the diameter d1 thereof is equal to or slightly less than the maximum diameter D of the tapered portion 10a of a round cross section. The thickness t1 of the electrode plate 12 and the thickness t2 of the adhesive 13 related to the diameter d1 of the equidiametric portion are determined such that when the electrode plates 12 are attached to the side surface with an adhesive 13, the diameter d2 of the equidiametric portion 10b having the electrode plates 12 attached thereto is not larger than the maximum diameter D of the tapered portion 10a (preferably equal to the maximum diameter D). Further, when the diameter d2 of the equidiametric portion 10b having the electrode plates 12 attached thereto is equal to the maximum diameter D of the tapered portion 10a, the width R of the outer surface side of the electrode plate 12 can be represented as R=D/2.

Figure 6A:
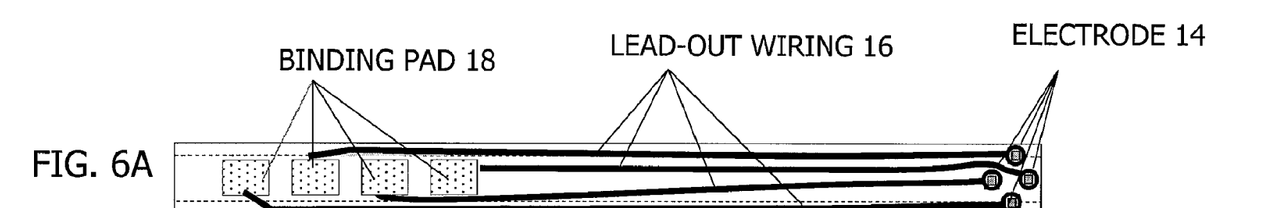
FIG. 6A and FIG. 6B illustrate the structure of the electrode plate 12.
Figure 6B:
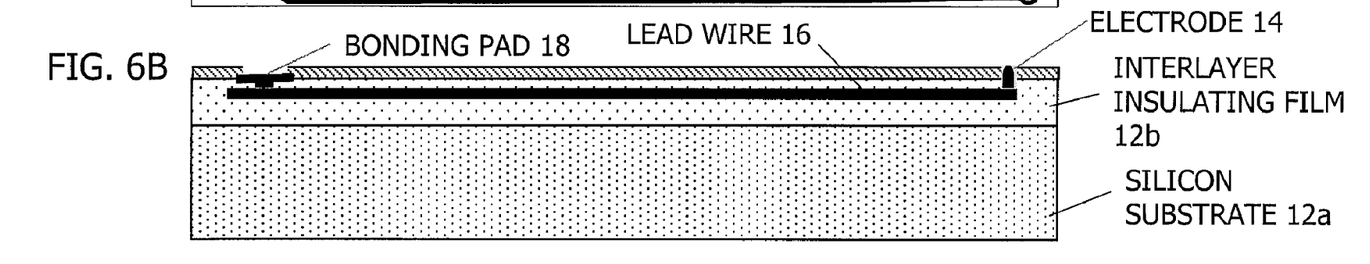

FIG. 6A and FIG. 6B illustrate the structure of the electrode plate 12. FIG. 6A is a cross-sectional view of the electrode plate 12 having four electrodes 14 and four bonding pads 18 connected to the electrodes 14 by lead-out wires 16. FIG. 6B is a cross-sectional view illustrating the wiring structure of the electrodes and bonding pads. The wiring in FIG. 6A is made visible to facilitate the explanation, but the wiring actually does not appear on the surface.

The electrode plate 12 has an interlayer insulating film 12b on a silicon substrate 12a. The electrodes 14, wirings 16, and bonding pads 18 are formed in the interlayer insulating film 12b. The electrode plate 12 can be manufactured by using a LSI manufacturing process. The process for manufacturing the electrode plate 12 will be described below.

The insulating substrate constituting the electrode plate 12 is not limited to the silicon substrate 12a and interlayer insulating film 12b, and a variety of insulating substrates using well-known insulating materials (alumina, ceramics, and the like) can be used. A configuration may be also used in which electrodes, wirings and terminals for external connection (bonding pads) are provided on the insulating substrate. In the present embodiment, since a LSI manufacturing process is used to manufacture the electrode plate 12, the use of a silicon substrate is assumed. A LSI that performs signal processing such as amplification and A/D conversion can be connected via a connector for electric connection to the bonding pads. Thus, by installing a chip-like LSI of an extremely compact shape in the root portion of the brain probe, it is possible to take out digital signals with a low level of noise from the brain probe itself, without using an external large signal processing device.

Figure 7A:
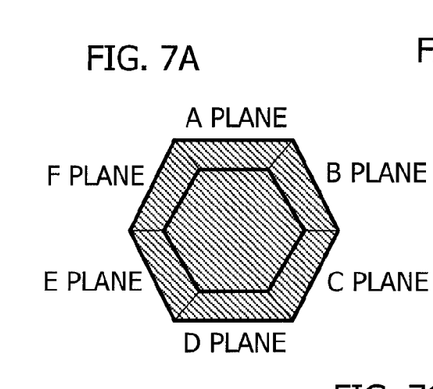
FIG. 7A to FIG. 7C show arrangement examples of the electrodes 14.
Figure 7B:
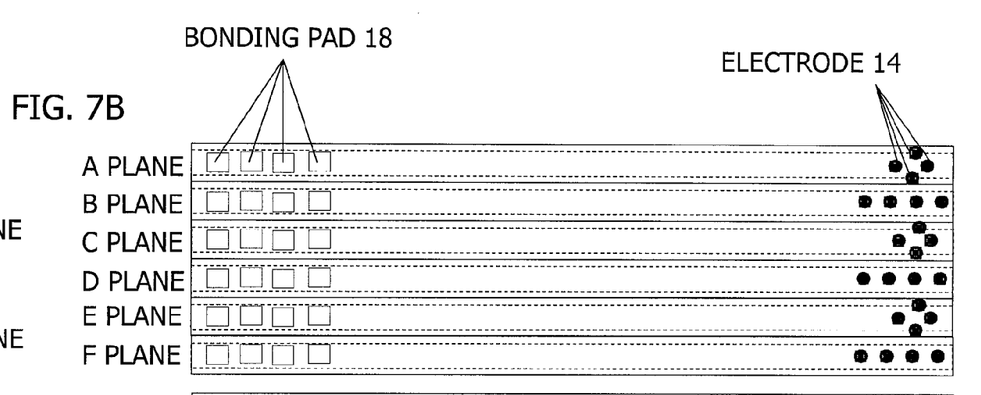
Figure 7C:
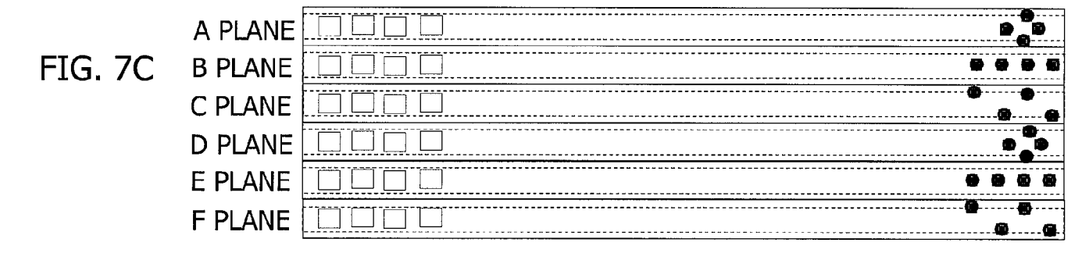

FIG. 7A to FIG. 7C illustrate an arrangement example of electrodes 14. Three arrangement patterns of the electrodes 14 are shown in FIG. 7B and FIG. 7C in relation to the case in which the hexagonal electrode plate 12 has planes A to F as shown in FIG. 7A.

FIG. 7B shows an example in which the electrodes are alternately arranged in two arrangement patterns, each pattern being located on one plane. More specifically, the first arrangement pattern in which four electrodes 14 are disposed in a rhomboidal configuration is located on planes A, C, and E, whereas the second arrangement pattern in which fourth electrodes 14 are arranged linearly in a row is located on planes B, D, and F. In the arrangement example shown in FIG. 7B, simultaneous measurements can be performed with the arrangement patterns of two kinds and each of the two arrangement patterns is disposed on three planes. Therefore, omnidirecitonal measurements can be performed with each arrangement pattern.

FIG. 7C illustrates an example in which three arrangement patterns are disposed in such a manner that the opposing surfaces have the same arrangement pattern. More specifically, the planes A and D have a first arrangement pattern in which four electrodes 14 are disposed a rhomboidal configuration, the planes B and E have a second arrangement pattern in which four electrodes 14 are arranged linearly in a row, and the planes C and F have a third arrangement pattern in which four electrodes 14 are arranged in the form of a parallelogram. In the arrangement example shown in FIG. 7C, simultaneous measurements can be conducted by the arrangement patterns of three kinds. It goes without saying that the planes A to E may have the same arrangement pattern, or all of the planes may have different arrangement patterns. When all of the six planes have the same arrangement pattern, three planes are sufficient to ensure omnidirecitonal configuration. Therefore, in the usual usage mode, a method can be used in which an electrode plate on one plane is used and the remaining electrode plates are in a standby state.

Further, the number of electrodes per one plane is not limited to four as shown in the figure, and no particular limitation is placed on the number of electrodes. Furthermore, different planes may have different numbers of electrodes. The arrangement patterns are also not limited to those shown in the figures, and other patterns can be used or combinations thereof can be determined as appropriate according to the measurement and stimulation location.

In addition, where as many electrodes as possible and lead-out wirings connected thereto are formed on one electrode plate and electric connection is performed by selecting electrodes for use, one electrode plate can be used with a variety of arrangement patterns.

Figure 8A:
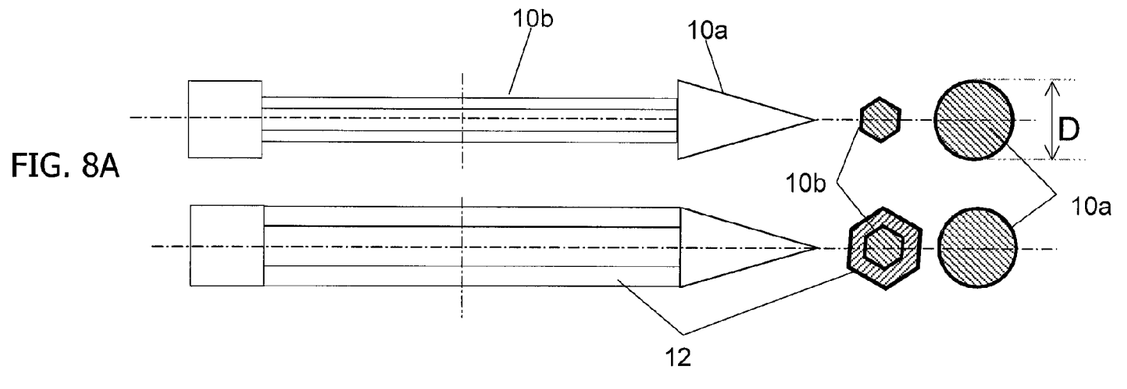
FIG. 8A and FIG. 8B show another configuration example of the brain probe in the embodiment of the embodiment of the present invention.
Figure 8B:
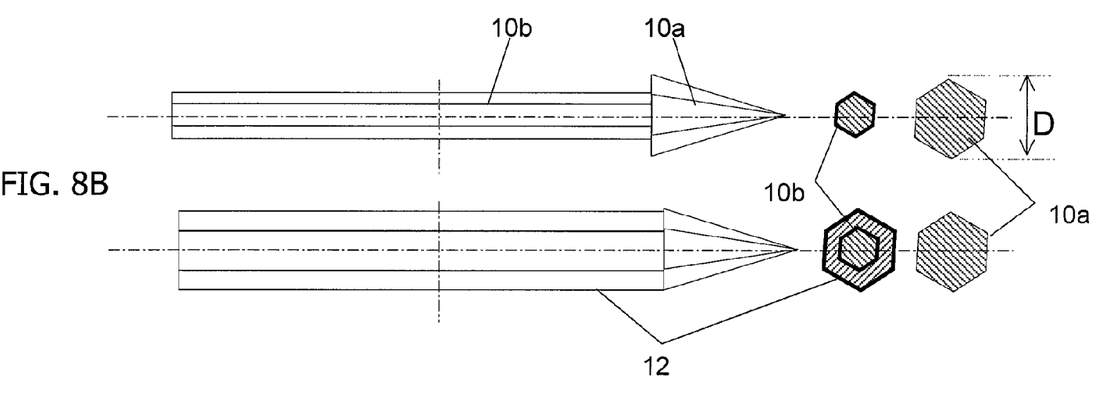

FIG. 8A and FIG. 8B show another configuration example of the brain probe of the embodiment of the present invention. By contrast with the configuration shown in FIG. 1A to FIG. 1C, in the configuration shown in FIG. 8A, part of the side surface of the equidiametric portion 10b of the core probe 10 is hexagonal and an electrode plate is attached to each plane. The tapered portion 10a has a conical shape similarly to that in the configuration shown in FIG. 1A to FIG. 1C. By contrast with the configuration shown in FIG. 1A to FIG. 1C, in the configuration shown in FIG. 8B, the tapered portion 10a is in the form of a hexagonal pyramid.

Figure 9:
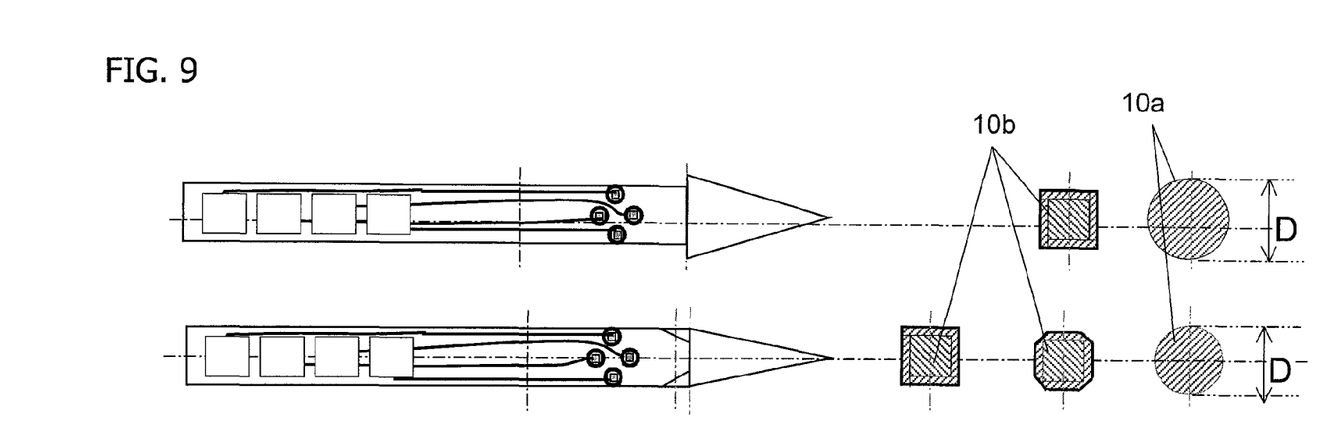
FIG. 9 shows a configuration example of the brain probe having four side planes.
Figure 10:
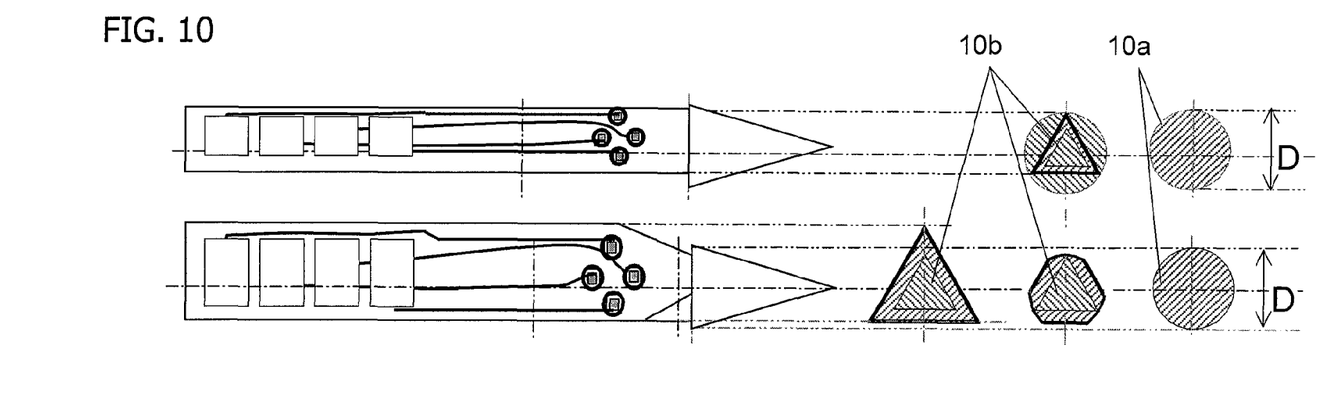
FIG. 10 shows a configuration example of the brain probe having three side planes.

FIG. 9 shows a configuration example of a brain probe having four side planes. FIG. 10 shows a configuration example of a brain probe having three side planes. The brain probe in accordance with the present invention is not limited to the configuration having the above-described six side planes and can have three or more planes. In FIG. 9, the equidiametric portion 10b has a square cross section and is attached to the core probe 10 so that four electrode plates 12 form four side planes. In FIG. 10, the equidiametric portion 10b has a regular triangular cross section and is attached to the core probe 10 so that three electrode plates form three side planes. Further, a step between the tapered portion 10a and the equidiametric portion 10b can be reduced by cutting obliquely the end portions of the electrode plates 12 as shown in FIG. 9B and FIG. 10B.

FIG. 11A to FIG. 11G and FIG. 12A to FIG. 12K illustrate a manufacturing process flow for the electrode plate 12. The electrode plate in the present embodiment is manufactured by using a LSI manufacturing process. Therefore, a silicon substrate is used as the insulating material. FIG. 11A to FIG. 11G show a manufacturing process flow for an electrode plate having no metal shield, and FIG. 12A to FIG. 12K show a manufacturing process flow for the electrode plate 12 including a metal shield.

Figure 11A:
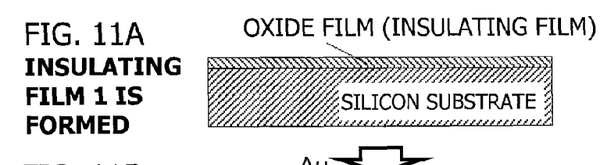
FIG. 11A to FIG. 11G illustrate the manufacturing process flow for the electrode plate 12.

First, in the process shown in FIG. 11A, an insulating film is formed on the surface of the silicon substrate. A silicon oxide film is formed by heating the silicon substrate to a high temperature and oxidizing the silicon substrate in an oxidizing atmosphere including oxygen. The silicon oxide film can be also produced by a CVD (Chemical Vapor Deposition) method.

Figure 11B:
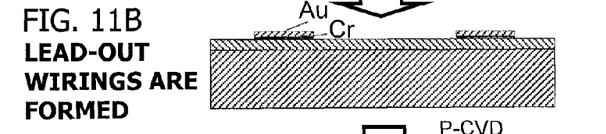

Then, in the process shown in FIG. 11B, the lead-out wirings are formed. More specifically, a Cr film and an Au film are formed by successively sputtering Cr and Al, and then the Au/Cr film is subjected to photolithographic treatment to form the wirings. Thus, a resist is coated on the Au/Cr film, a wiring pattern mask is transferred onto the resist by exposure, and then the unnecessary Au/Cr film is removed by etching, and finally the remaining resist present on the Au/Cr film is removed.

Figure 11C:
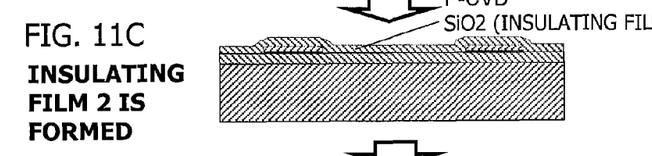

Then, in the process shown in FIG. 11C, an insulating film is further formed on the silicon oxide film so as to cover the Au/Cr film formed as the lead-out wirings. The insulating film is formed, for example, by depositing a silicon oxide film ($SiO_2$) by plasma CVD (P-CVD).

Figure 11D:
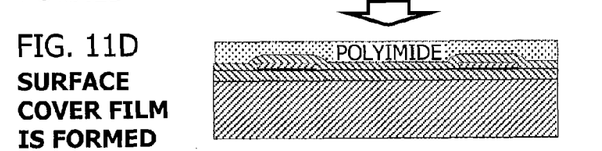

Then, in the process shown in FIG. 11D, a surface cover film is formed. The surface cover film is formed, for example, by spin coating a polyimide film.

Figure 11E:
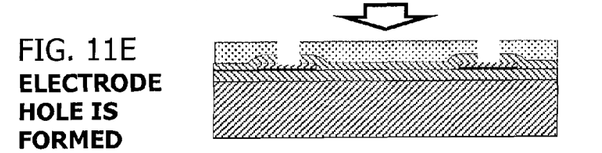

Then, in the process shown in FIG. 11E, electrode holes are formed. The electrode holes are formed by a photolithographic process. Thus, a resist is coated on a polyimide coat, a mask pattern corresponding to the formation positions of electrode holes is transferred to the resist by exposure, and the polyimide resin and insulating film (film formed in the process shown in FIG. 11C) are removed by etching, and the Au/Cr film is exposed. Finally, the remaining resist is removed.

Figure 11F:
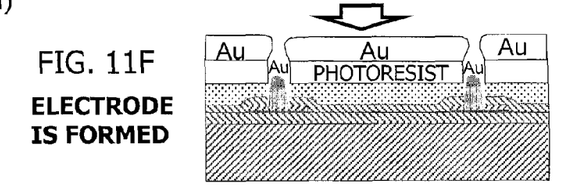

Then, in the process shown in FIG. 11F, the electrodes are formed. More specifically, a resist is coated on the surface of the polyimide resin from which the portions where the Au/Cr film is exposed have been removed, and then a gold film is formed by vapor deposition. The gold film is deposited to a thickness such that gold deposited on the exposed portions of the Au/Cr film, which are electrode formation positions, protrudes from the surface of the polyimide resin.

Figure 11G:
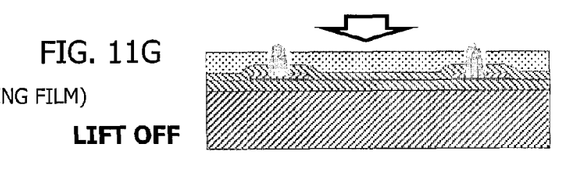

Finally, in the process shown in FIG. 11G, the resist is removed (lift off) together with the gold film deposited on the resist. The electrode plate having electrodes and lead-out wirings is thus manufactured. The formed electrodes include electrodes for signal detection (or signal output) on the brain probe tip side and electrodes for connection to the bonding pads on the other end side, and the electrodes on both sides can be formed in the same process by the above-described manufacturing process flow. The manufacturing process flow shown in FIG. 12A to FIG. 12K will be explained below. The manufacturing process flow shown in FIG. 12A to FIG. 12K is obtained by adding the processes relating to the formation of a metal shield (processes shown in FIG. 12D, FIG. 12E, FIG. 12F, and FIG. 12G) to the manufacturing process flow shown in FIG. 11A to FIG. 11G.

Figures 12A, 12B, 12C, 12D, 12E, 12F, 12G, 12H, 12I, 12J, 12K:
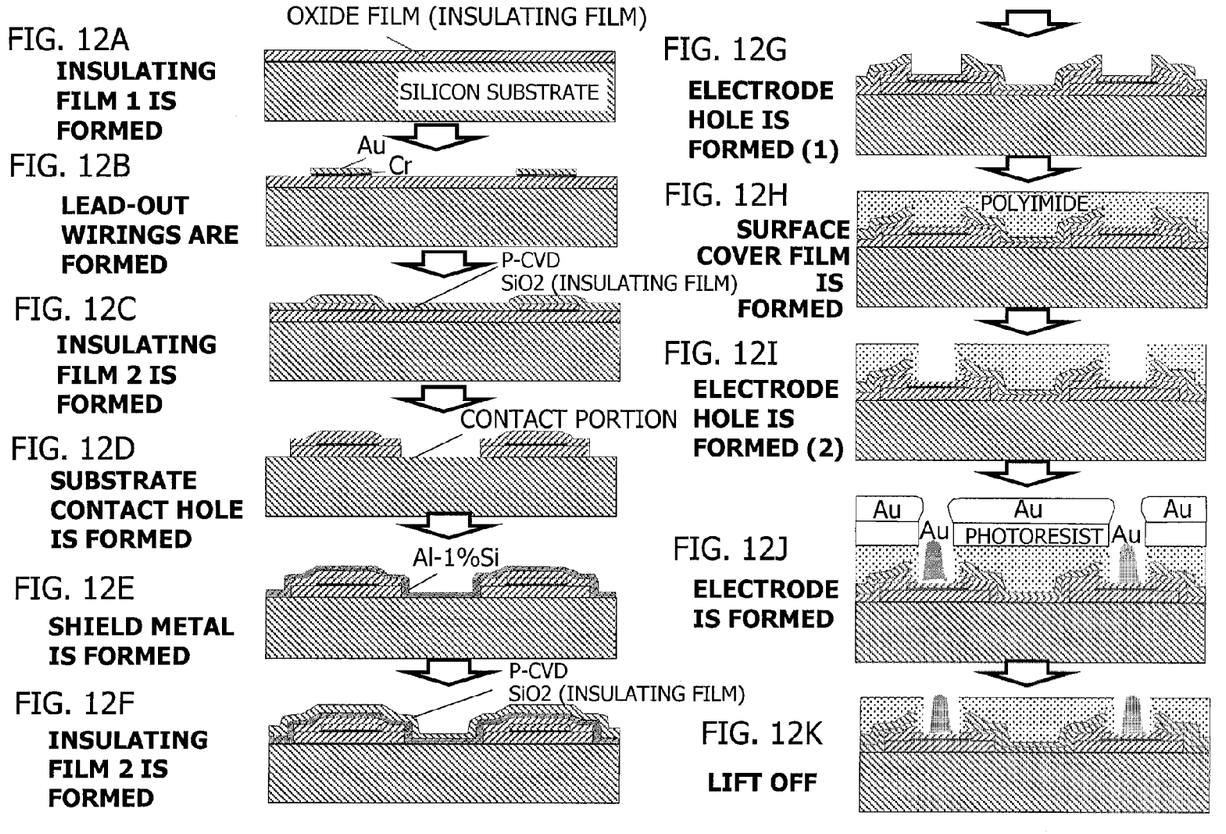
FIG. 12A to FIG. 12K illustrate the manufacturing process flow for the electrode plate 12 (provided with the shield metal).

Explaining the flow in the order of performance, first, in the process shown in FIG. 12A, an insulating film is formed on the surface of a silicon substrate in the same manner as in the process shown in FIG. 11A. A silicon oxide film is formed by heating the silicon substrate to a high temperature and oxidizing the silicon substrate in an oxidizing atmosphere including oxygen. The silicon oxide film can be also produced by a CVD (Chemical Vapor Deposition) method.

Then, in the process shown in FIG. 12B, lead-out wirings are formed in the same manner as in the process shown in FIG. 11B. More specifically, a Cr film and an Au film are formed by successively sputtering Cr and Al, and then the Au/Cr film is subjected to photolithographic treatment to form the wirings. Thus, a resist is coated on the Au/Cr film, a wiring pattern mask is transferred onto the resist by exposure, and then the unnecessary Au/Cr film is removed by etching, and finally the resist present on the remaining Au/Cr film is removed.

Then, in the process shown in FIG. 12C, an insulating film (inner insulating film) is further formed on the silicon oxide film so as to cover the Au/Cr film formed as the lead-out wirings, in the same manner as in the process shown in FIG. 11C. The inner insulating film is formed, for example, by depositing a silicon oxide film by plasma CVD.

Then, in the process shown in FIG. 12D, substrate contact holes are formed. A resist is coated, a mask with a pattern of contact portions is transferred to the resist by exposure, and then the silicon oxide film in the contact portions is removed by etching. The resist remaining on the insulating film is then removed.

Then, in the process shown in FIG. 12E, a shield metal is formed. The shield metal material is, for example, Al-1% Si. Sputtering is used to form the shield metal film.

Then, in the process shown in FIG. 12F, an insulating film (outer insulating film) is further formed on the shield metal so as to cover the shield metal. The outer insulating film is formed by depositing a silicon oxide film by plasma CVD in the same manner as in the process shown in FIG. 12C.

Then, in the process shown in FIG. 12G, electrode holes are formed. The electrode holes are formed by a photolithographic process. Thus, a resist is coated on the insulating film, a mask pattern corresponding to the formation positions of electrode holes is transferred by exposure to the resist, and then the outer insulating film, shield metal, and inner insulating film in the formation positions of contact holes are removed by etching, and the Au/Cr film is exposed. Finally, the remaining resist is removed.

Then, in the process shown in FIG. 12H, a surface cover film is formed in the same manner as in FIG. 11D. The surface cover film is formed, for example, by spin coating a polyimide film.

Then, in the process shown in FIG. 12I, electrode holes are formed after coating a polyimide film, in the same manner as in FIG. 11E. The electrode holes are formed by a photolithographic process. Thus, a resist is coated on a polyimide coat, a mask pattern corresponding to the formation positions of electrode holes is transferred to the resist by exposure, the polyimide resin in the formation positions of electrode holes is removed by etching, and the Au/Cr film is exposed. Finally, the remaining resist is removed.

Then, in the process shown in FIG. 12J, the electrodes are formed in the same manner as in FIG. 11F. More specifically, a resist is coated on the surface of the polyimide resin from which the portions where the Au/Cr film is exposed have been removed, and then a gold film is formed by vapor deposition. The gold film is deposited to a thickness such that gold deposited on the exposed portions of the Au/Cr film, which are electrode formation positions, protrudes from the surface of the polyimide resin.

Finally, in the process shown in FIG. 12K, the resist is removed (lift off) together with the gold film deposited on the resist in the same manner as in FIG. 11G. The electrodes and lead-out wirings are thus formed and the electrode plate having a shield metal is thus manufactured.

Figures 13A, 13B:
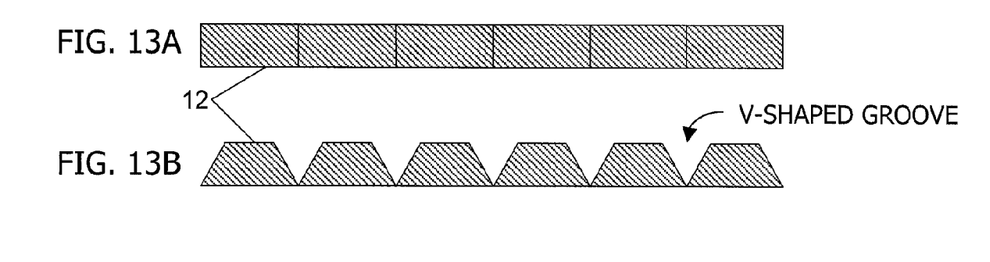
FIG. 13A to FIG. 13E illustrate the manufacturing process for six electrode plates 12 connected by the long side portions.

FIG. 13A to FIG. 13E illustrate a process for manufacturing six electrode plates 12 connected by the long side portions thereof. By manufacturing six electrode plates 12 connected by the long side portions thereof, as shown in the above-described FIG. 4A to FIG. 4C, it is possible to wind the six electrode plates 12 about the side planes of the core probe 10 and attach the electrode plates to the side planes. In order to manufacture the six electrode plates 12 connected by the long side portions thereof, first, electrodes and lead-out wirings of the electrode plates are produced side by side according to the above-described manufacturing process flow on one silicon substrate having a surface area corresponding to six electrode plates (FIG. 13A). A processing is then performed to form V-shaped grooves between the electrode plates so that the electrode plates have a substantially trapezoidal cross section, while maintaining the state in which the bottom portions of the electrode plates are connected at a predetermined thickness level (FIG. 13B). Only the cross-sectional shape of the electrode plates is shown in FIG. 13A and FIG. 13B, and constituent elements such as electrodes are omitted.

Figure 13C:
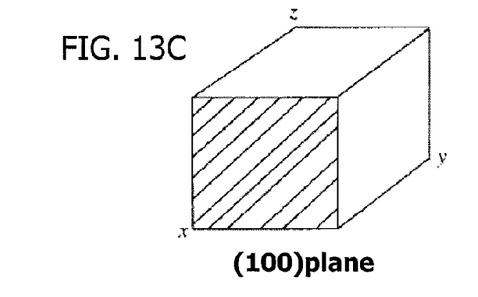
Figure 13D:
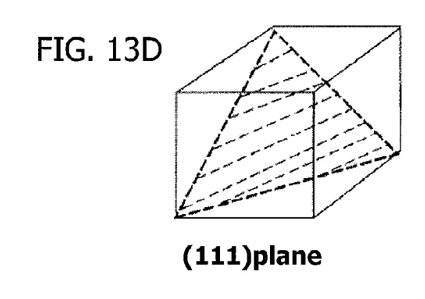
Figure 13E:
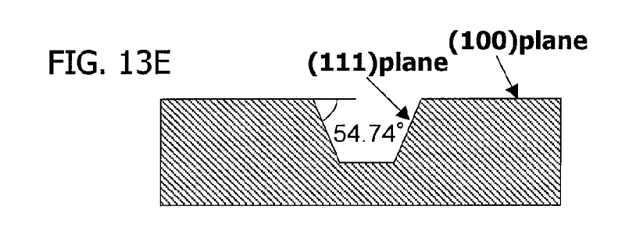

The processing in which the V-shaped grooves are formed uses anisotropic etching of single crystal silicon. The anisotropic etching is an etching process using the difference in etching rate between the crystallographic planes of silicon. By using the fact that the etching rate of the (111) plane (FIG. 13D) is much lower than that of the (100) plane (FIG. 13C) of a silicon crystal and etching the (100) plane as shown in FIG. 13E), it is possible to form the V-shaped grooves in the depth direction. The angle in this case is 54.74 degrees. This angle is very close to an angle of 60 degrees between the trapezoids when a regular hexagonal shape is produced by six electrode plates. Therefore, six electrode plates 12 having a cross-sectional shape making it possible to form a regular hexagon can be manufactured.

Figures 14A, 14B:
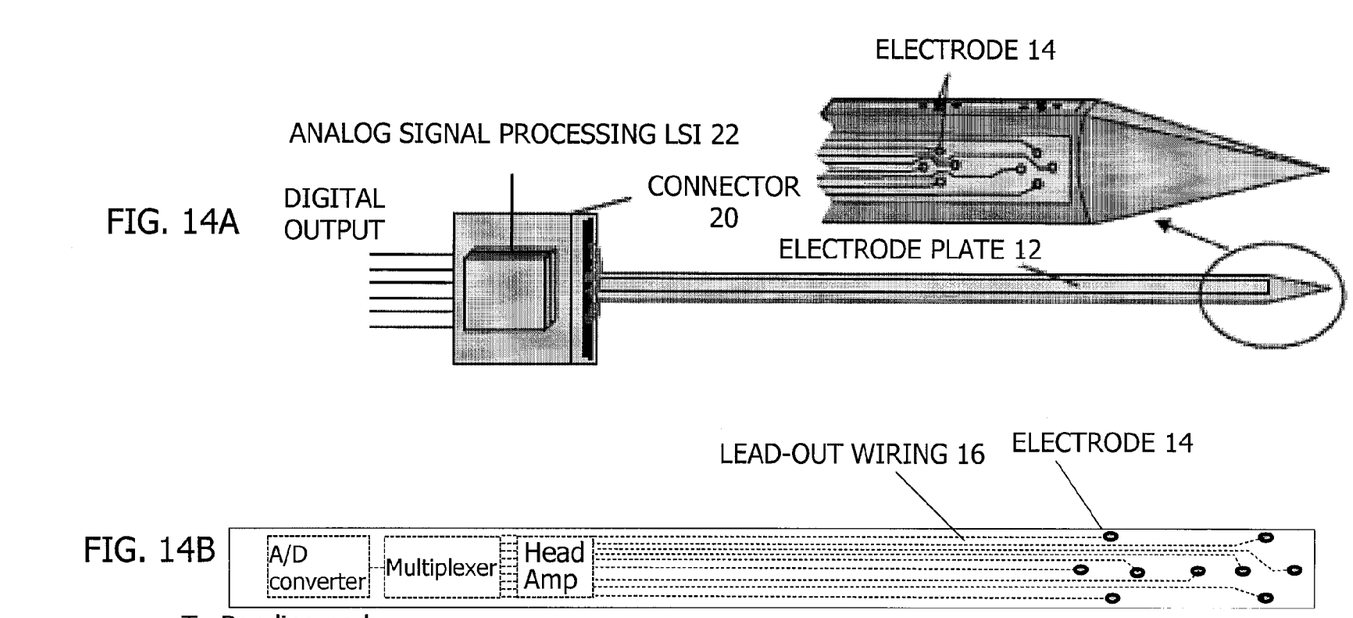
FIG. 14A to FIG. 14C illustrate the arrangement of the signal processing circuit connected to the electrodes.

FIG. 14A to FIG. 14C illustrate the arrangement of the signal processing circuit that is connected to the electrodes. FIG. 14A shows a configuration in which an analog signal processing LSI 22 is attached to the brain probe by a connector 20 that is electrically connected to the electrodes 14 at the base portion of the brain probe. The analog signal processing LSI is a chip including various signal processing circuits such as an A/D converter, a multiplexer, a head amplifier, and a filter circuit and is electrically connected to the connector 20. The analog signal processing LSI 22 performs a predetermined signal processing, such as amplification, of analog signals from the electrodes 14, converts the signals into digital signals, and outputs the digital signals. The analog signal processing LSI also converts the digital electric signals sent to the electrodes 14 into analog signals, performs predetermined signal processing, and outputs the processed signals to the electrodes 14.

Figure 14C:
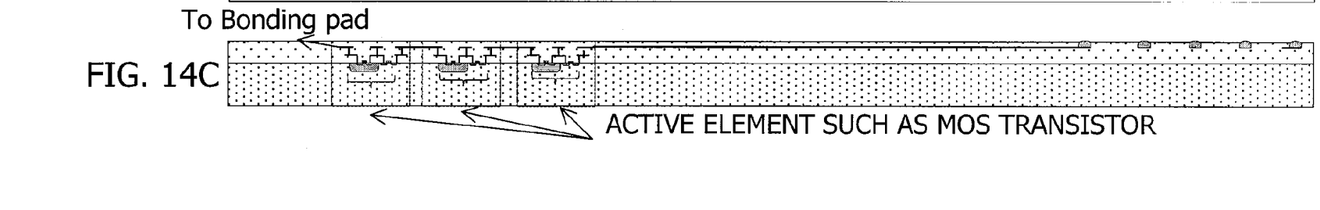

FIG. 14B and FIG. 14C show a configuration in which the signal processing circuit is formed directly on the electrode plate 12. FIG. 14B and FIG. 14C are respectively a plan view and a cross-sectional view of the electrode plate 12 having the signal processing circuit formed thereon. In addition to the operations of constituting the electrode plate 12 by a silicon substrate and forming the electrodes 14 and lead-out wirings 16 on the silicon substrate, as described hereinabove, active elements, such as MOS transistors, constituting the signal processing circuit such as an A/D converter, a multiplexer, and a head amplifier, are formed directly on the silicon substrate. The signal processing circuit is incorporated in the brain probe itself and the signal processing circuit and brain probe can be manufactured integrally.

In the brain probe of the embodiment of the present invention, the core is constituted by a hard core probe. Therefore, the auxiliary tube is unnecessary, the core can be individually inserted to the basal ganglia in the deep portion of cerebrum, and invasiveness thereof is very low. In addition, three or more electrode plates make it possible to obtain an omnidirecitonal probe. Furthermore, since the brain signals are received by three or more electrode plates, the brain signal generation position can be specified by the difference in reception levels between the electrode plates.

Even if the position stimulated by the electrodes is that of effective action, it is still possible that side effects will be produced. Since the omnidirecitonal brain probe makes it possible to provide stimulation by adjusting positions with all orientations with one brain probe, the most effective position stimulation can be performed without multiple insertions or the insertion or multiple probes, and the effective treatment can be performed without damaging the brain.

The brain probe of the present embodiment is optimum for measuring brain activity and electrically stimulating the brain, as described hereinabove, but this electrode probe for living body can be also applied to body portions other than the brain.

INDUSTRIAL APPLICABILITY

The present invention can be applied to an electrode probe for insertion into the brain in a device that measures brain waves and a device that provides electric stimulation to brain cells.

The invention claimed is:

1. A brain probe comprising:
a core probe made of a metal; and
n electrode plates attached so as to cover an entire side surface circumference of the core probe, and forming n side planes providing an n-angular cross section (n is an integer equal to or greater than 3), wherein
at least one electrode and a lead-out wiring extending in a longitudinal direction of the side plane from each of the at least one electrode are provided at each of the electrode plates.

2. The brain probe according to claim 1, wherein
the core probe has a tapered portion that is tapered to a tip and an equidiametric portion extending from the tapered portion toward the other end of the core probe, a diameter of the equidiametric portion is less than a maximum diameter of the tapered portion, and a diameter of the equidiametric portion in which the electrode plates have been covered on the side surface of the equidiametric portion of the core probe is substantially equal to or less than the maximum diameter of the tapered portion.

3. The brain probe according to claim 1, wherein each electrode plate has a silicon substrate.

4. The brain probe according to claim 1, wherein n is 6.

5. The brain probe according to claim 1, wherein
each of the n electrode plates is either a first electrode plate having a plurality of electrodes arranged in a first arrangement pattern or a second electrode plate having a plurality of electrodes arranged in a second arrangement pattern different from the first arrangement pattern.

6. The brain probe according to claim 5, wherein
when n is 6, the first electrode plate and the second electrode plate are arranged alternatively on the core probe so as to form three side planes of the first electrode plate and three side planes of the second electrode plate.

7. The brain probe according to claim 1, wherein
each of the n electrode plates is either a first electrode plate having a plurality of electrodes arranged in a first arrangement pattern, a second electrode plate having a plurality of electrodes arranged in a second arrangement pattern different from the first arrangement pattern, and a third electrode plate having a plurality of electrodes arranged in a third arrangement pattern different from the first arrangement pattern and the second arrangement pattern.

8. The brain probe according to claim 7, wherein
when n is 6, a pair of the first electrode plates, a pair of the second electrode plates, and a pair of the third electrode plates are arranged on the core probe, with the paired plates of the same type facing each other.

9. The brain probe according to claim 1, further comprising a signal processing circuit that performs predetermined signal processing with respect to signals from the electrodes and signals outputted to the electrodes, and is connected to the lead-out wirings extending from the electrodes.

10. The brain probe according to claim 9, wherein
each electrode plate has a silicon substrate, and the signal processing circuit is formed on the silicon substrate.

11. A method for manufacturing a brain probe comprising the steps of:
manufacturing n (n is an integer equal to or greater than 3) electrode plates, each having at least one electrode and a lead-out wiring extending from each of the at least one electrode; and
attaching the n electrode plates to an entire side surface circumference of a metal core probe so as to form n side planes providing an n-angular cross section (n is an integer equal to or greater than 3).

12. The method for manufacturing a brain probe according the claim 11, wherein
the n electrode plates are manufactured to be connected by long side portions thereof and attached by winding on the side surface of the core probe.

13. The method for manufacturing a brain probe according the claim 11, wherein
the n electrode plates are manufactured to be connected by long side portions thereof by using a silicon substrate, and grooves are formed by anisotropic etching at boundaries between adjacent electrode plates.

14. The method for manufacturing a brain probe according the claim 11, wherein
the n electrode plates are manufactured by using a silicon substrate, and a signal processing circuit that performs predetermined signal processing with respect to signals from the electrodes and signals outputted to the electrodes and is connected to the lead-out wirings extending from the electrodes is formed on the silicon substrate of each of the electrode plates.

* * * * *